United States Patent [19]

Khokhar

[11] Patent Number: 5,041,578
[45] Date of Patent: Aug. 20, 1991

[54] WATER SOLUBLE 1,2-DIAMINOCYCLOHEXANE PLATINUM (IV) COMPLEXES AS ANTITUMOR AGENTS

[75] Inventor: Abdul R. Khokhar, Houston, Tex.

[73] Assignee: Board of Regents, The University of Texas System, Austin, Tex.

[21] Appl. No.: 274,824

[22] Filed: Nov. 22, 1988

[51] Int. Cl.$^5$ .................. C07F 15/00; A61K 31/28
[52] U.S. Cl. .................................................. 556/137
[58] Field of Search ........................ 556/137; 514/492

[56] References Cited

U.S. PATENT DOCUMENTS

| | | |
|---|---|---|
| 3,904,663 | 9/1975 | Tobe . |
| 4,115,418 | 9/1978 | Gale . |
| 4,137,248 | 1/1979 | Gale et al. ................... 260/429 R |
| 4,140,707 | 2/1979 | Cleare . |
| 4,169,846 | 10/1979 | Kidani . |
| 4,203,912 | 5/1980 | Hydes et al. ................... 260/429 R |
| 4,225,529 | 9/1980 | Hydes et al. ................... 260/429 R |
| 4,230,631 | 10/1980 | Hydes et al. ................... 260/429 R |
| 4,256,652 | 3/1981 | Kidani et al. ................... 260/429 R |
| 4,271,085 | 6/1981 | Amundsen et al. ............ 260/429 R |
| 4,431,666 | 2/1984 | Bulten . |
| 4,466,924 | 8/1984 | Verbeek . |
| 4,657,927 | 3/1987 | Cleare . |
| 4,661,516 | 4/1987 | Brown et al. ................... 514/492 |
| 4,680,308 | 7/1978 | Schwartz . |
| 4,760,155 | 7/1988 | Heffernan . |
| 4,760,156 | 7/1988 | Heffernan . |
| 4,760,157 | 7/1988 | Child . |
| 4,845,124 | 7/1989 | Kidani et al. ................... 514/492 |
| 4,861,905 | 8/1989 | Nowatari et al. ............... 556/40 |

FOREIGN PATENT DOCUMENTS

| | | |
|---|---|---|
| 898614 | 1/1984 | Belgium . |
| 113508 | 11/1983 | European Pat. Off. . |
| 130482 | 6/1984 | European Pat. Off. . |
| 136012 | 8/1984 | European Pat. Off. . |
| 0147926 | 10/1985 | European Pat. Off. . |
| 193936 | 3/1986 | European Pat. Off. . |
| 0237450 | 4/1987 | |
| WO87/02364 | 4/1987 | PCT Int'l Appl. . |
| WO88/03925 | 6/1988 | PCT Int'l Appl. . |
| 2160867 | 6/1985 | United Kingdom . |

OTHER PUBLICATIONS

Vollano, J. F., et al., Comparative Antitumor Studies on Platinum (II) and Platinum (IV) Complexes Containing 1,2-Diaminocyclohexane, J. Med. Chem. 1987, vol. 30, No. 4, p. 716-719.
Printout from Dialog Search.
Perez-Soler et al., Cancer Research, 47:6462-6466 (Dec. 1987).
Maeda, et al., Japan Journal Cancer Research (Gaann, 77:523-525) (Jun., 1986).
Kihari, Chemical Abstracts 105:134160X.
Craciunescu, Eur., J. Med. Chem. 353-357 (1984).
Sur, Oncology 40:372-376 (1983).
Freise, Archives Internationales de Pharmacodynamie et de Therapie No. 258-No. 2, Aug. 1982.
Kaledin, Jncl. vol. 66, No. 5, May 1981.
Delicoonstantinos, Biochem. Soc. Trans. 5(5):1326-1329 (1977).
Yatvin, Proc. Am. Assoc. Cancer Res. 21:281 (1980).
Schwartz, Chemical Abstracts, 88:16014K (1978).
Perez-Soler, Cancer Research 46, 6269-6273 (1986).
Connors, Chem. Biol. Interactions, 5:415-424 (1972).
Ridgway, J. Clin. Hematol. Oncol. 7:220-229 (1977).
Burchenal, Chemical Abstracts 93:1125661t (1980).
Appleton, Chemical Abstracts 101:182656c (1984).
Speer, Chemical Abstracts 84:54030n (1976).
Khokhar, Chemical Abstracts 103:226308p (1980).
Tzu, Chemical Abstracts 94:218774t (1981).

*Primary Examiner*—Arthur C. Prescott
*Assistant Examiner*—S. Jervey
*Attorney, Agent, or Firm*—Arnold, White & Durkee

[57] ABSTRACT

Water-soluble complexes having the formula:

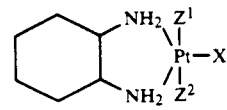

and stereoisomers thereof, where $Z^1$ and $Z^2$ are halogens and X is selected from the group consisting of sulfate, phosphate, nitrate, monocarboxylate, and dicarboxylate, have been found to have desirable antitumor activity, as well as relatively low levels of toxicity.

10 Claims, No Drawings

WATER SOLUBLE 1,2-DIAMINOCYCLOHEXANE PLATINUM (IV) COMPLEXES AS ANTITUMOR AGENTS

The U.S. government may own certain rights in this invention pursuant to National Cancer Institute grant No. RO1-CA-41581.

FIELD OF THE INVENTION

The present invention relates to platinum based drugs and methods of using such drugs and formulations thereof in antitumor therapy.

BACKGROUND OF THE INVENTION

Some platinum based drugs are known to have useful antitumor activity. However, such drugs are also known to have various drawbacks. For example, cisplatin is one such drug with a significant level of activity, but which also exhibits significant nephrotoxicity. Other platinum drugs have been synthesized which have less potential to cause renal injury, but many of these drugs are much less soluble in water than is desirable.

A long standing need exists for platinum drugs which will have improved aqueous solubility and antitumor activity, a broader spectrum of activity against various neoplastic disease states, and also a lack of cross resistance to other antitumor drugs such as cisplatin.

SUMMARY OF THE INVENTION

The present invention includes complexes having the formula

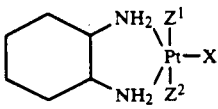

and stereoisomers thereof, where $Z^1$ and $Z^2$ are halogens and X is selected from the group consisting of sulfate, phosphate, nitrate, monocarboxylate, and dicarboxylate. In a preferred embodiment, X is selected from the group consisting of malonate, cycloalkanemonocarboxylate, cycloalkenemonocarboxylate, cycloalkanedicarboxylate, and cycloalkenedicarboxylate.

Another embodiment of the present invention concerns complexes having the formula

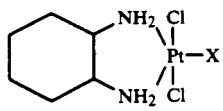

and stereoisomers thereof, where X is selected from the group consisting of 1,1-cyclobutanedicarboxylate, cyclobutanemonocarboxylate, and malonate. In yet another aspect, the present invention relates to trans-dichloro (1,2-diaminocyclohexane) platinum (IV) complexes, where the complex additionally includes a ligand selected from the above-mentioned group.

The present invention also concerns antitumor compositions which include an effective amount of one or more above-described compounds, and a pharmaceutically acceptable carrier. Additionally, the present invention concerns methods of inhibiting neoplastic cell growth, which include the step of administering to a mammal an effective amount of one or more of the above-described complexes.

The complexes, compositions, and methods of the present invention possess significant advantages over the prior art. Platinum (IV) complexes in accordance with the present invention possess high aqueous solubility, high antitumor activity, a broad spectrum of activity, and a lack of cross resistance to other antitumor drugs such as cisplatin. Therefore, the complexes, compositions, and methods of the present invention are believed to have significant therapeutic advantages in the treatment of neoplastic disease states.

DETAILED DESCRIPTION OF THE SPECIFIC EMBODIMENTS

Specific examples of complexes in accordance with the present invention include the following:

| Complex No. | Complex Name |
|---|---|
| 1. | Trans-dichloro(1,1-cyclobutanedicarboxylato) (trans-1,2-diaminocyclohexane) platinum (IV) |
| 2. | Trans-dichloro(1,1-cyclobutanedicarboxylato) (trans-R,R-1,2-diaminocyclohexane) platinum (IV) |
| 3. | Trans-dichloro(1,1-cyclobutanedicarboxylato) (trans-S,S-1,2-diaminocyclohexane) platinum (IV) |
| 4. | Trans-dichloro(1,1-cyclobutanedicarboxylato) (cis-1,2-diaminocyclohexane) platinum (IV) |
| 5. | Trans-dichloro(cyclobutanecarboxylato) (OH) (trans-1,2-diaminocyclohexane) platinum (IV) |
| 6. | Trans-dichloro(malonato) (cis, trans-1,2-diaminocyclohexane) platinum (IV) |

An example of the synthesis of a complex in accordance with the present invention is as follows.

The reaction was initiated by the addition of a solution of potassium iodide (28 g, 168 mmol in 50 ml of water) to a filtered aqueous solution of $K_2PtCl_4$ (12 g, 28.9 mmol) in 200 ml of water. Trans-R,R-1,2-diaminocyclohexane (DACH) (3.5 g, 30.7 mmol) in 10 ml of water was added dropwise to the solution of $K_2PtI_4$ and stirring was continued for one hour at room temperature. The brown solid, cis-diiodo-DACH-platinum (II), was removed by filtration and washed successively with $H_2O$, methanol, and ether. After the final product was dried under vacuum, the final yield was 86%.

To prepare the water-soluble sulfato-DACH-platinum, cis-diiodo-DACH-platinum (II) (16.88 g, 0.03 mol) was added to a solution of $Ag_2SO_4$ (8.88 g, 0.0285 mol) in 1800 ml of water. The reaction mixture was stirred overnight at room temperature (protected from light) and the precipitated AgI was removed by filtration. The yellow solution was evaporated to dryness at 45° C. under reduced pressure. A yellow product was obtained which was further purified from water. The yield of sulfato-DACH-platinum was 95%.

DACH-Pt-1,1-cyclobutanedicarboxylate was synthesized by dissolving sulfato-DACH-platinum (0.5447 g) in 20 ml of water and adding to it sodium 1,1-cyclobutanedicarboxylate prepared in situ by the addition of 0.5 ml of 5N NaOH and 0.187 g of 1,1-cyclobutanedicarboxylic acid in 10 ml of water. The reaction mixture was stirred at room temperature for 20 hours, and the white precipitate was separated by filtration and washed with cold water, ethanol, and ether. The final product was recrystallized from water. Hydrogen peroxide (4 ml, 30%) was added to a suspension of DACH-Pt-1,1-cyclobutanedicarboxylate (0.64 g in 100 ml of water). The reaction mixture was left stirring for one hour at 45° C. The clear solution was filtered and the volume of the filtrate was reduced to about 3 ml, and white precipitate was separated by filtration, washed with 3×2 ml of cold water, acetone, ether, and dried under vacuum to give a yield of 91%.

Trans-dichloro(DACH)Pt(IV)-1,1-cyclobutanedicarboxylate was synthesized by adding 125 ml of 0.02N HCl (0.723 mg/ml) to a suspension of DACH-Pt(IV) (OH)$_2$1,1-cyclobutanedicarboxylate (0.606 g in 10 ml of water), and leaving the suspension stirring for 30 minutes at room temperature. The light yellow solution was filtered, and the volume of the filtrate was reduced under vacuum to 2 ml. The light yellow product was separated by filtration, washed with 2×2 ml of cold water, and dried under vacuum to give 78% of the final product.

The above mentioned procedure can be used to synthesize compounds in accordance with the present invention. Cyclobutanemonocarboxylic acid or malonic acid can be substituted for 1,1-cyclobutanedicarboxylic acid in this procedure.

Analytical and spectroscopic data for the six complexes listed above are given in Tables 1 and 2, respectively.

TABLE 1

| Complex No. | Observed % | | | Calculated (%) | | |
|---|---|---|---|---|---|---|
| | C | H | N | C | N | N |
| 1 | 27.87 | 4.1 | 5.09 | 26.67 | 4.07 | 5.18 |
| 2 | 25.83 | 4.42 | 4.72 | 25.80 | 4.30 | 5.01 |
| 3 | 26.11 | 4.66 | 4.69 | 25.80 | 4.30 | 5.01 |
| 4 | 24.83 | 4.29 | 4.69 | 25.80 | 4.30 | 5.01 |
| 5 | 26.61 | 4.43 | 5.64 | 26.90 | 4.70 | 5.01 |
| 6 | 22.08 | 3.51 | 5.76 | 22.00 | 3.46 | 5.70 |

TABLE 2

| Complex No. | $\nu\, C = O(cm^{-1})$ | $\nu\, C = O(cm^{-1})$ |
|---|---|---|
| 1 | 1660, 1628 | 1345 |
| 2 | 1660, 1628 | 1345 |
| 3 | 1660, 1628 | 1344 |
| 4 | 1660, 1628 | 1345 |
| 5 | 1660 | 1363 |
| 6 | 1655, 1639 | 1345 |

The antitumor activity of complexes in accordance with the present invention was tested by injecting L1210 murine leukemia cells (100,000) intraperitoneally into BDF1 mice on day 0. The six above-listed compounds, as well as cisplatin, were injected intraperitoneally on days 1, 5, and 9 at dose levels ranging from 1.56 mg/kg to 200 mg/kg. Table 3 below gives for each complex the optimal dose that appeared from this test, as well as the percent T/C (median survival time of treated mice/median survival time of control mice×100)

TABLE 3

| Complex | Optimal Dose (mg/kg) | % T/C |
|---|---|---|
| 1 | 50 | 253 |
| 2 | 50 | 471 (2/5)* |
| 3 | 100 | 329 (1/5) |
| 4 | 100 | 388 (1/5) |
| 5 | 12.5 | 388 (2/5) |
| 6 | 50 | 167 |

TABLE 3-continued

| Complex | Optimal Dose (mg/kg) | % T/C |
|---|---|---|
| Cisplatin | 3 | 218 |

*Numbers in parentheses indicates number of animals cured/number of animals treated.

The spectrum of antitumor activity of platinum complex number 1 was tested by injecting four different types of murine tumor cells intraperitoneally into BDF1 mice on day 0. One hundred thousand cells were injected for L1210 and L1210/cisplatin, while 1,000,000 Cells were injected for M5076, and 0.5 ml of a 10% brei for B-16. Complex 1 (25 mg/kg) or cisplatin (3 mg/kg) were injected on days 1, 5, and 9 in the case of L1210, 1210/cisplatin, and B-16, and on days 1, 5, 9, and 13 for M5076. The results of this test are shown in Table 4.

TABLE 4

| Murine Tumor Model | % T/C | |
|---|---|---|
| | Complex 1 | Cisplatin |
| L1210 | 171 | 218 |
| L1210/cisplatin | 167 | 94 |
| B-16 | 232 | 139 |
| M5076 | 197 (1/5)* | 265 |

*Numbers in parentheses indicates number of animals cured/number of animals treated.

Compositions in accordance with the present invention can suitably include a pharmaceutically effective amount of one or more platinum complexes in accordance with the present invention, and a pharmaceutically acceptable carrier, such as, for example, water, saline, or dextrose solution. Compositions in accordance with the present invention will contain between about 0.001% and about 99% by weight active complexes, preferably between about 0.001% and about 10%.

Methods in accordance with the present invention comprise administering to a mammal an effective amount of the compounds or compositions described above. The administering step can suitably be parenteral and by intravenous, intraarterial, intramuscular, intralymphatic, intraperitoneal, subcutaneous, intrapleural, or intrathecal injection, or by topical application or oral dosage. Such administration is preferably repeated on a timed schedule until tumor regression or disappearance has been achieved, and may be used in conjunction with other forms of tumor therapy such as surgery or chemotherapy with different agents.

The description and examples given in this patent are intended to illustrate the present invention. They are not intended to be an exhaustive list of all possible specific embodiments of the present invention. Those skilled in the art will recognize that modifications could be made to the specific embodiments listed here which would still be within the scope of the present invention.

We claim:

1. A platinum complex selected from the group consisting of trans-dichloro(1,1-cyclobutanedicarboxylato) (trans-1,2-diaminocyclohexane) platinum (IV), trans-dichloro(1,1-cyclobutanedicarboxylato) trans-R,R-1,2-diaminocyclohexane) platinum (IV), trans-dichloro(1,1-cyclobutanedicarboxylato) (trans-S,S 1,2-diaminocyclohexane) platinum (IV), trans-dichloro(1,1-cyclobutanedicarboxylato) (cis 1,2-diaminocyclohexane) platinum (IV).

2. An anti-tumor composition which includes an effective amount of a platinum complex selected from the group consisting of trans-dichloro(1,1-cyclobutanedicarboxylato) (trans-1,2-diaminocyclohexane) platinum (IV), trans-dichloro(1,1-cyclobutanedicarboxylato) trans-R,R-1,2-diaminocyclohexane) platinum (IV), trans-dichloro(1,1-cyclobutanedicarboxylato) (trans-S,S-1,2-diaminocyclohexane) platinum (IV), transdichloro(1,1-cyclobutanedicarboxylato) (cis-1,2-diaminocyclohexane) platinum (IV); and a pharmaceutically acceptable carrier.

3. Trans-dichloro(1,1-cyclobutanedicarboxylato) (trans-1,2-diaminocyclohexane) platinum (IV).

4. Trans-dichloro(1,1-cyclobutanedicarboxylato) (trans-R,R-1,2-diaminocyclohexane) platinum (IV).

5. Trans dichloro(1,1-cyclobutanedicarboxylato) trans-S,S-1,2-diaminocyclohexane) platinum (IV).

6. Trans-dichloro(1,1-cyclobutanedicarboxylato) (cis-1,2-diaminocyclohexane) platinum (IV).

7. An antitumor composition which includes an effective amount of trans-dichloro(1,1-cyclobutanedicarboxylato) (trans-1,2-diaminocyclohexane)platinum (IV); and a pharmaceutically acceptable carrier.

8. An antitumor composition which includes an effective amount of trans-dichloro(1,1-cyclobutanedicarboxylato) (trans-R,R-1,2-diaminocyclohexane) platinum (IV); and a pharmaceutically acceptable carrier.

9. An antitumor composition which includes an effective amount of trans-dichloro(1,1-cyclobutanedicarboxylato) (trans-S,S-1,2-diaminocyclohexane) platinum (IV); and a pharmaceutically acceptable carrier.

10. An antitumor composition which includes an effective amount of trans-dichloro(1,1-cyclobutanedicarboxylato) (cis-1,2-diaminocyclohexane) platinum (IV); and a pharmaceutically acceptable carrier.

* * * * *

UNITED STATES PATENT AND TRADEMARK OFFICE
CERTIFICATE OF CORRECTION

PATENT NO. : 5,041,578

DATED : August 20, 1991

INVENTOR(S) : Abdul R. Khokhar, et al.

It is certified that error appears in the above-identified patent and that said Letters Patent is hereby corrected as shown below:

At column 4, line 63, there should be a parentheses before the word "trans".

At column 4, line 65, between "S,S" and "1,2" there should be a hyphen.

Signed and Sealed this

Twelfth Day of January, 1993

Attest:

DOUGLAS B. COMER

Attesting Officer

Acting Commissioner of Patents and Trademarks